United States Patent [19]

Paritee et al.

[11] 3,956,399

[45] May 11, 1976

[54] HALOGENATED-METHYLBENZYL PHENYL ETHERS

[75] Inventors: Frederick Paritee; John A. Alford; Charles E. Reineke, all of Midland, Mich.

[73] Assignee: The Dow Chemical Company, Midland, Mich.

[22] Filed: Oct. 16, 1970

[21] Appl. No.: 81,496

[52] U.S. Cl. .................... 260/612 R; 260/613 R; 260/520 C; 260/479 R; 260/465 F; 260/465 G; 260/512 C; 260/45.85 R; 260/45.9 NC; 260/45.7 R

[51] Int. Cl.$^2$ .......................................... C07C 43/20

[58] Field of Search ................................ 260/612 R

[56] References Cited

UNITED STATES PATENTS

| | | | |
|---|---|---|---|
| 2,073,010 | 3/1937 | Holt | 260/612 R |
| 2,109,456 | 3/1938 | Bass et al. | 260/612 R |
| 2,109,457 | 3/1938 | Bass et al. | 260/612 R |
| 2,109,514 | 3/1938 | Van Duzee et al. | 260/612 R |
| 2,121,723 | 6/1938 | Bass et al. | 260/612 R |
| 2,121,724 | 6/1938 | Bass et al. | 260/612 R |

OTHER PUBLICATIONS

Hart et al., Jour. Org. Chem., Vol. 23 (1958), pp. 2019–2020.

*Primary Examiner*—Bernard Helfin
*Attorney, Agent, or Firm*—Ralph M. Mellom

[57] ABSTRACT

Halogenated α-methylbenzyl phenyl ethers have been found to be excellent fire retardants for thermoplastics such as polystyrene and polypropylene.

5 Claims, No Drawings

HALOGENATED-METHYLBENZYL PHENYL ETHERS

BACKGROUND OF THE INVENTION

The invention relates to new compounds that are adjacent homologues of known compounds which have been employed as fire retardants in thermoplastics. These known compounds, halogenated phenyl benzyl ethers, are described by Sauer et al. in U.S. Pat. No. 3,250,739. These compounds differ from those of the present invention by only an α-methyl group. Yet this difference gives the compounds of the invention an unexpected advantage as a fire retardant.

As a general rule, compounds become more suited to use as fire retardants by the addition of more halogen. The present invention, however, adapts a known compound of the art, the halogenated benzyl phenyl ether, to use as a fire retardant by adding more hydrocarbon. Since hydrocarbon lends more fuel for the fire, it would be expected that the compounds of the invention containing similar amounts of halogen would be inferior to the known compounds described by Sauer et al. This, however, is not true. As shown by the comparative examples in the Specific Embodiments, the compounds of the invention act more efficiently as a fire retardant in thermoplastic substrates.

In the search for a suitable fire retardant for thermoplastics, it has been discovered that some samples of a thermoplastic containing a fire retardant behave differently in a low temperature flame, such as that of a paper match, than they do in a high temperature flame, such as that of a Bunsen burner. The ability of fire retardants to act in low temperature flames is very important for most sources of flame which cause significant fire hazards are low temperature flames. Thus, a desirable fire retardant must be efficient in extinguishing a low temperature flame while at the same time providing adequate protection against high temperature flames.

SUMMARY OF THE INVENTION

It has now been found that new compounds corresponding to the formula

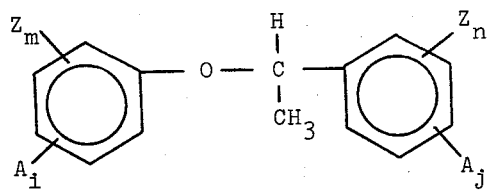

wherein
each Z is independently Br or Cl
$m$ and $n$ are integers of 1–5
each A is independently an inert substituent, such as F, I, methyl, phenyl, hydroxy, methoxy, nitro, carboxy, acetoxy, cyano or sulfo
$i$ and $j$ are integers of 0–2 where $i<m$ and $j<n$ and more than 50% by weight of the compound is Br, Cl or mixture thereof
meet the criteria of a desirable fire retardant for thermoplastics. Furthermore, these compounds are more efficient in controlling low temperature flames than the compounds of the art while at the same time producing a more desirable product, especially in polystyrene.

The compounds of the invention may be any of those described by the general formula above. The compounds are conveniently prepared by reacting the appropriate α-haloethylbenzene with the appropriate alkali metal phenate to obtain the compound of the formula above where the benzyl portion of the ether has the substituents of the ethylbenzene and the phenyl portion of the ether has the substituents of the phenate. The positioning of the substituents on the aromatic ring does not substantially affect the fire retardancy of the compounds; therefore, in reference to these compounds, the placement of the substituents will not usually be given. Also, for purposes of simplicity in giving representative examples, the basic structure, the α-methylbenzyl phenyl ether, will be omitted and only the substituents will be named. For example, bromo bromo would be ar-bromo-α-methylbenzyl bromophenyl ether. Using this nomenclature, representative examples of the compounds of the invention include: bromo pentabromo; pentabromo bromo; tribromo tribromo; trichloro trichloro; chloro dibromo; trichloro bromochloro; dibromochloro tribromo; dichlorotribromo dibromo; tribromodimethyl trichloro; dibromofluoro tribromo; phenyltribromo hydroxydichloro; tetrabromonitro dichlorocarboxy; bromocyano tetrabromo; and dibromosulfo trichloroacetoxy.

Preferred compounds of the invention contain as substituents only bromine and chlorine, i.e., where $i=j=0$ and compounds wherein either of the aromatic rings contains three or more bromine or chlorine substituents, i.e., where $m$ or $n=3-5$. Of special interest in the invention are those compounds containing bromine, i.e., where each Z is Br, with those compounds containing 6–8 bromines being of particular importance because of their special effectiveness.

The compounds of the invention may be incorporated into any thermoplastic in any amount that will give effective fire retardancy. This amount varies widely as different thermoplastics are employed but generally a substrate containing about 0.1 to about 20% by weight of the compound has a desirable degree of fire retardancy, with amounts of about 1 to about 10 percent by weight being preferred.

The thermoplastic to which the fire retardants may be added vary widely. Essentially any thermoplastic may be used as the substrate so long as it can be processed at temperatures which are below the decomposition point of the fire retardant. Representative examples of suitable thermoplastics include: polyolefins such as polystyrene, polypropylene and polyethylene; saturated and unsaturated polyesters, acrylics and polyamides. Of these thermoplastics, the addition of the fire retardants to polyolefins, especially polystyrene and polypropylene, is of special importance because of the desirable fire retardant product obtained.

The fire retardants of the invention may be used alone or in combination with other known fire retardants, synergists or stabilizers. Other known fire retardants include chlorinated and brominated aliphatic and aromatic compounds and halogenated phosphorus compounds. The primary synergists of importance are antimony oxide and red phosphorus although other known synergists may also be employed. Stabilizers for the compounds, such as barium cadmium soaps, trialkyl phosphates and organo tin compounds may also be employed to deter discoloration.

The fire retardant along with other additives, if any, is conveniently incorporated into the thermoplastic by softening or melting the thermal plastic and then mechanically incorporating the fire retardant into the polymer. Although the preferrd method involves the mixing of a melt of the thermoplastic and a melt of the fire retardant, solid mixtures of the fire retardant and thermoplastic may also be prepared. By either method, the product obtained is a desirable fire resistant material having physical and chemical properties similar to that of the original thermoplastic.

SPECIFIC EMBODIMENTS

Example 1 — Preparation of 2,4,5-tribromo-α-methylbenzyl 2,4,6-tribromophenyl ether In a reactor was placed 330.8 g. (1.0 mole) of 2,4,6-tribromophenol, 138.2 g. (1.0 mole) of $K_2CO_3$, 421.8 g. (1.0 mole) of α, 2,4,5-tetrabromoethylbenzene and 1000 ml. of dimethylformamide. The mixture was stirred at room temperature for 2 hours and poured into 1000 ml. of water. The resulting precipitate was filtered and washed with 500 ml. of water and then 500 ml. of 70% methanol-water. The white solid obtained was recrystallized from a chloroform-hexane mixture to give 660.5 g. of a product having a melting point of 110.5°–112°C.

Examples 2–5 and Comparative Examples A–D — Use in Polypropylene

Fire retardants of the invention were compared in polypropylene to the known compounds shown by Sauer et al. in U.S. Pat. No. 3,250,739. A melt of the fire retardant and a general purpose polypropylene was mixed in a Brabender mixer for 5 minutes and molded. The products were tested using the standard test ASTM-635 with a Bunsen burner and with a vertical match test. In the vertical match test, a sample measuring 5 × ¼ × ⅛ inch is vertically suspended and ignited with a paper match until the match is burned up. The time (S.E.) is measured. The recorded times are the average of 3 tests on each of 2 samples. In addition, the samples were examined to determine the Limiting Oxygen Index (L.O.I.) as described in Combustion and Flame 10, 135 (1966). The compounds tested and results of these tests are shown in Table I.

TABLE I

Comparison of the Compounds of the Invention to the Compounds of the Art in Polypropylene

| Example | Compound | % Halogen | L.O.I. | ASTM-635 S.E., sec. | Vertical Match S.E., sec. |
|---|---|---|---|---|---|
| Comp. A | (tribromophenyl-OCH₂-tribromophenyl) | 5 | 0.24 | 3 | 11.6 |
| 2 | (tribromophenyl-C(CH₃)(OCH)-tribromophenyl) | 5 | 0.24 | <1 | <1 |
| Comp. B | (phenyl-Br₅ — O-CH₂ — tribromophenyl) | 1 | 0.24 | 3.0 | 6.7[1] |
| Comp. C | " | 3 | 0.25 | 1.2 | 6.7 |
| Comp. D | " | 5 | 0.25 | | 4.3 |
| 3 | (phenyl-Br₅ — O-CH(CH₃) — tribromophenyl) | 1 | 0.26 | 1.8 | 5.6[1] |
| 4 | " | 3 | 0.28 | 1.2 | 2.1 |
| 5 | " | 5 | 0.26 | | 1.1 |

[1]Average of three tests on each of three samples

Examples 6–9 and Comparative Examples E–H — Use in Polystyrene

In parallel experiments, the compounds of the invention were compared in high impact and general purpose polystyrene to those shown by Sauer et al. in U.S. Pat. No. 3,250,739. In each of the tests, the fire retardant was incorporated into polystyrene in an amount sufficient to give the percentage of halogen shown in Table I. The test samples were prepared by melting the polystyrene and fire retardant in a Brabender mixer, adding the fire retardant and mixing for 5 minutes at 180°C. The melt was molded and samples were cut and subjected to any one or combination of three tests: Underwriters Laboratory test UL-94 using a Bunsen burner; UL-94 modified by the substitution of a paper match for the Bunsen burner; and the vertical match test. The samples were further tested by observation to determine the transparency of the resulting material. The samples of general purpose polystyrene using the compounds of the invention showed significantly better transparency than the samples containing the art compounds, especially at higher loadings. The compounds tested for fire retardancy and the results are shown in Table II.

Examples 10–18 — Use of Fire Retardants in Other Thermoplastics

In a manner similar to that shown above, a fire retardant of the invention was tested in other thermoplastics. The test employed involved 20 sequential ignitions of two separate samples measuring 1 × ½ × 9 inches inclined at a 30° angle below horizontal in a draft-free enclosure. The ignition was caused by contact of a gas flame 1 inch high applied at the lower end of the sample for five seconds. The gas flame was removed and the time to self-extinguish was noted. Immediately after the flame on the sample was extinguished, ignition was repeated in the same manner until termination of the 20 ignitions. The fire retardant employed was 2,4,5-tribromo-α-methyl-benzyl 2,4,6-tribromophenyl ether.

TABLE II

Comparison of Compounds of the Invention with the Homologues of the Art in Polystyrene

| Example | Compound | % Halogen | L.O.I. | Vertical Match[1] S.E., sec. | UL-94 S.E., sec. | UL-94 Match S.E., sec. |
|---|---|---|---|---|---|---|
| High Impact Polystyrene |  |  |  |  |  |  |
| Comp. E | 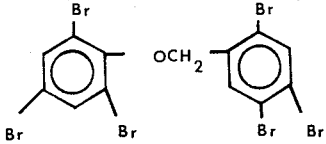 | 5 | 0.24 |  | 11–13 | Consumed |
| 6 | 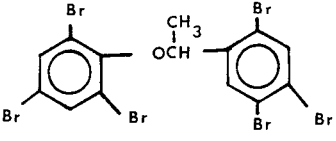 | 5 | 0.24 |  | <1 | <1 |
| General Purpose Polystyrene |  |  |  |  |  |  |
| Comp. F | 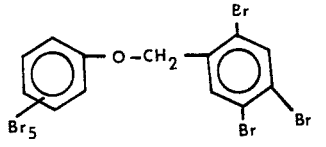 | 1 | 0.24 | 4.7 |  |  |
| Comp. G |  | 3 | 0.26 | 0.7 |  |  |
| Comp. H |  | 5 | 0.27 | 0.3 |  |  |
| General Purpose Polystyrene |  |  |  |  |  |  |
| 7 | 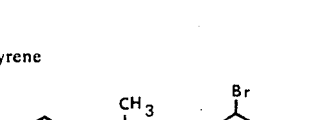 | 1 | 0.25 | 1.1 |  |  |
| 8 |  | 3 | 0.28 | 0.6 |  |  |
| 9 |  | 5 | 0.28 | 0.2 |  |  |

[1]Average of three tests on each of two samples

The thermoplastics tested, the loadings of the additive in parts per hundred parts of resin (p.p.h.) and result of the self-extinguishing tests given as an average value for the tests on the two samples are shown in Table II

TABLE III

Use of the Fire Retardant in Various Thermoplastics

| Example | Thermoplastic | Additive Level, p.p.h. | Time to S.E., sec. |
|---|---|---|---|
| 10 | High impact polystyrene sold under the trade name Styron 475 | 3.9 | 0.1 |

TABLE III-continued
Use of the Fire Retardant in Various Thermoplastics

| Example | Thermoplastic | Additive Level, p.p.h. | Time to S.E., sec. |
|---|---|---|---|
| 11 | Rubberized styrene-acrylonitrile sold under the trade name Tybrene 500 | 10 | 0.9 |
| 12 | 4% vinyl acetate copolymer with ethylene | 15 | 10 |
| 13 | General purpose polypropylene | 1 | 6.7 |
| 14 | General purpose polypropylene | 3 | 2.8 |
| 15 | General purpose polypropylene | 6 | 1.4 |
| 16 | General purpose polypropylene | 9 | 0.5 |
| 17 | Poly(methyl methacrylate) | 9.8 | 6.7 |
| 18 | General purpose polystyrene | 3 | 0 |

In the same manner as shown by the examples above, other compounds of the invention are prepared and incorporated into polystyrene or polypropylene. Also, in the same manner, the compounds of the examples above or other compounds of the invention are incorporated into other thermoplastics, such as polyethylene, saturated polyester unsaturated polyester or the various nylons in an amount that will effectively retard the burning of the resulting product.

We claim:
1. A compound of the general formula

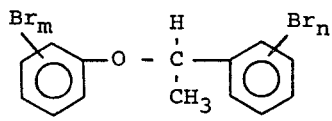

wherein
   $m$ and $n$ are integers of 1–5
   and more than about 50% by weight of the compound is Br.
2. The compound of claim 1 wherein $m$=3–5.
3. The compound of claim 1 wherein $n$=3–5.
4. The compound of claim 1 which contains 6–8 bromines.
5. The compound of claim 1 wherein $m$ is 5 and $n$ is 3.

* * * * *